(12) United States Patent
Geyer et al.

(10) Patent No.: US 10,246,733 B2
(45) Date of Patent: Apr. 2, 2019

(54) ASSAY AND METHOD FOR QUANTITATING CARBONIC ANHYDRASE ACTIVITY AND ASSESSING RED BLOOD HEMOLYSIS

(71) Applicant: CASE WESTERN RESERVE UNIVERSITY, Cleveland, OH (US)

(72) Inventors: Ryan R. Geyer, Cleveland, OH (US); Pan Zhao, Cleveland, OH (US); Mark D. Parker, Cleveland, OH (US); Walter F. Boron, Cleveland, OH (US)

(73) Assignee: CASE WESTERN UNIVERSITY, Cleveland, OH (US)

( * ) Notice: Subject to any disclaimer, the term of this patent is extended or adjusted under 35 U.S.C. 154(b) by 0 days.

(21) Appl. No.: 15/174,445

(22) Filed: Jun. 6, 2016

(65) Prior Publication Data

US 2016/0355867 A1    Dec. 8, 2016

Related U.S. Application Data

(60) Provisional application No. 62/170,972, filed on Jun. 4, 2015.

(51) Int. Cl.
*C12Q 1/527* (2006.01)

(52) U.S. Cl.
CPC ...... *C12Q 1/527* (2013.01); *C12Y 402/01001* (2013.01); *G01N 2333/988* (2013.01)

(58) Field of Classification Search
CPC .................................................. C12Q 1/527
See application file for complete search history.

(56) References Cited

U.S. PATENT DOCUMENTS

2015/0133405 A1    5/2015 Pelletier et al.

OTHER PUBLICATIONS

Crandall et al. J. Membrane Biol., 1982, 65:139-145.*
Ripoche, et al. PNAS, 2004, 49:17222-17227.*
Zhao, Jinhua, et al., "Out-of-equilibrium CO2/HCO-3 Solutions and their use in Characterizing a new K/HCO3 cotransporter", Nature, vol. 374, Apr. 13, 1995.
Cardenas, Victor, Jr., "Kinetics of Co2 Excretion and Intravascular pH Disequilibria During Carbonic Anhydrase Inhibition", The American Physiological Society, 1998, pp. 683-694.
Itada, Nobutomo, et al., "Carbonic Anhydrase Activity in Intact Red Blood Cells Measured with 18O Exchange", The Journal of Biological Chemistry, vol. 252, No. 11, Issue of Jun. 10, pp. 3881-3890, 1977.
Stemler, Alan, "An Assay for Carbonic Anhydrase Activity and Reactions that Produce Radiolabeled Gases or Small Uncharged Molecules", Analytical Biochemistry 210, 328-331 (1993).
Boyarsky, Gregory, et al. "pH regulation in single glomerular mesangial cells I. Acid extrusion in absence and presense of HCO-3", The American Physiological Society, 1998, pp. C844-C856.

* cited by examiner

*Primary Examiner* — Bin Shen
(74) *Attorney, Agent, or Firm* — Tarolli, Sundheim, Covell & Tummino LLP

(57) ABSTRACT

A method and assay for using carbonic anhydrase (CA), particularly CA-I or CA-II, as a biomarker of hemolysis. The method and assay detect hemolysis by determining a percentage erythrocyte hemolysis in a specimen or sample of blood based upon quantification of carbonic anhydrase present in the extracellular portion of the blood. The method and test serve to optimize therapeutic efficacy for treatments of hemolysis.

18 Claims, 9 Drawing Sheets

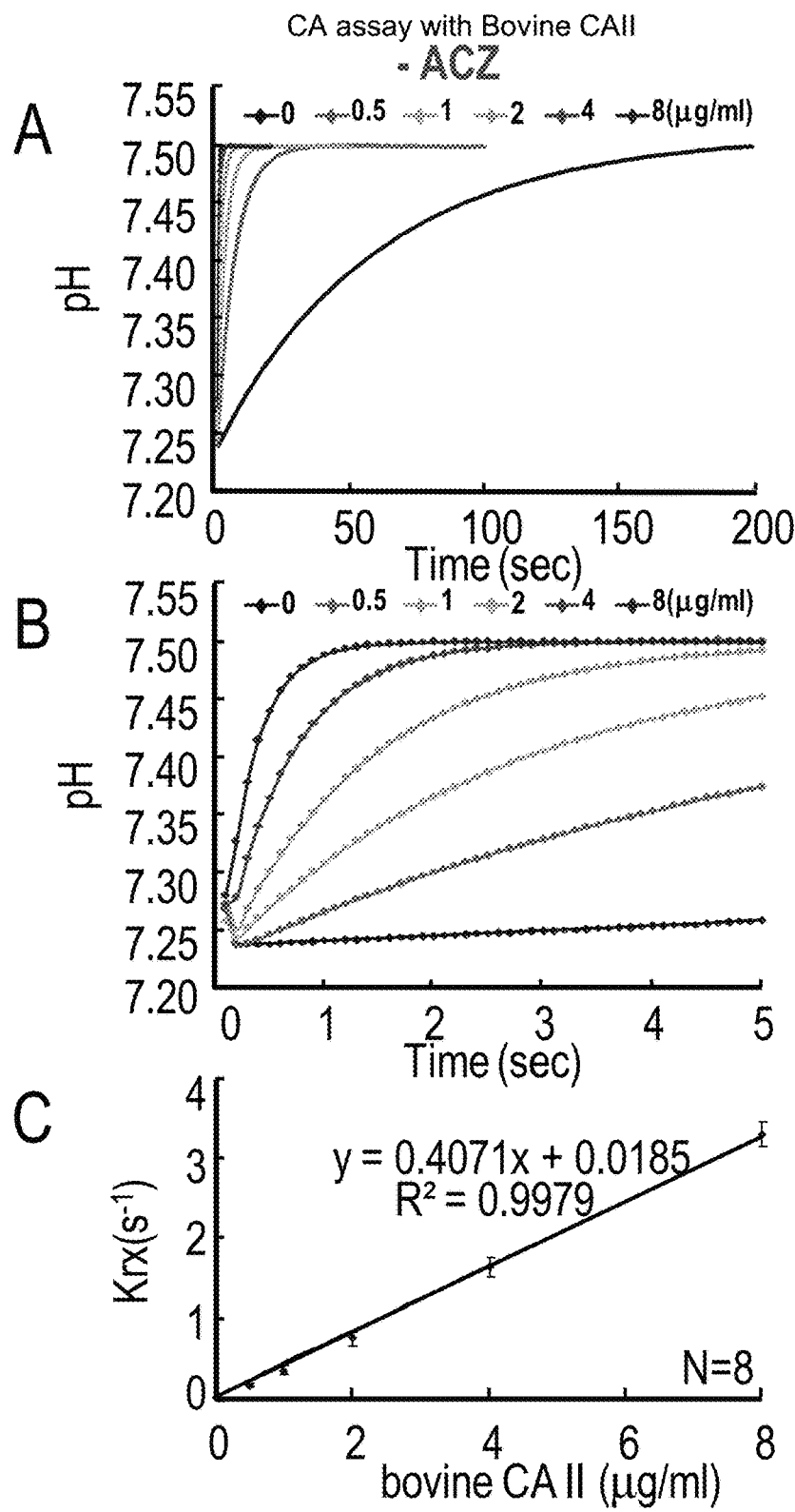
Figs. 2A-C

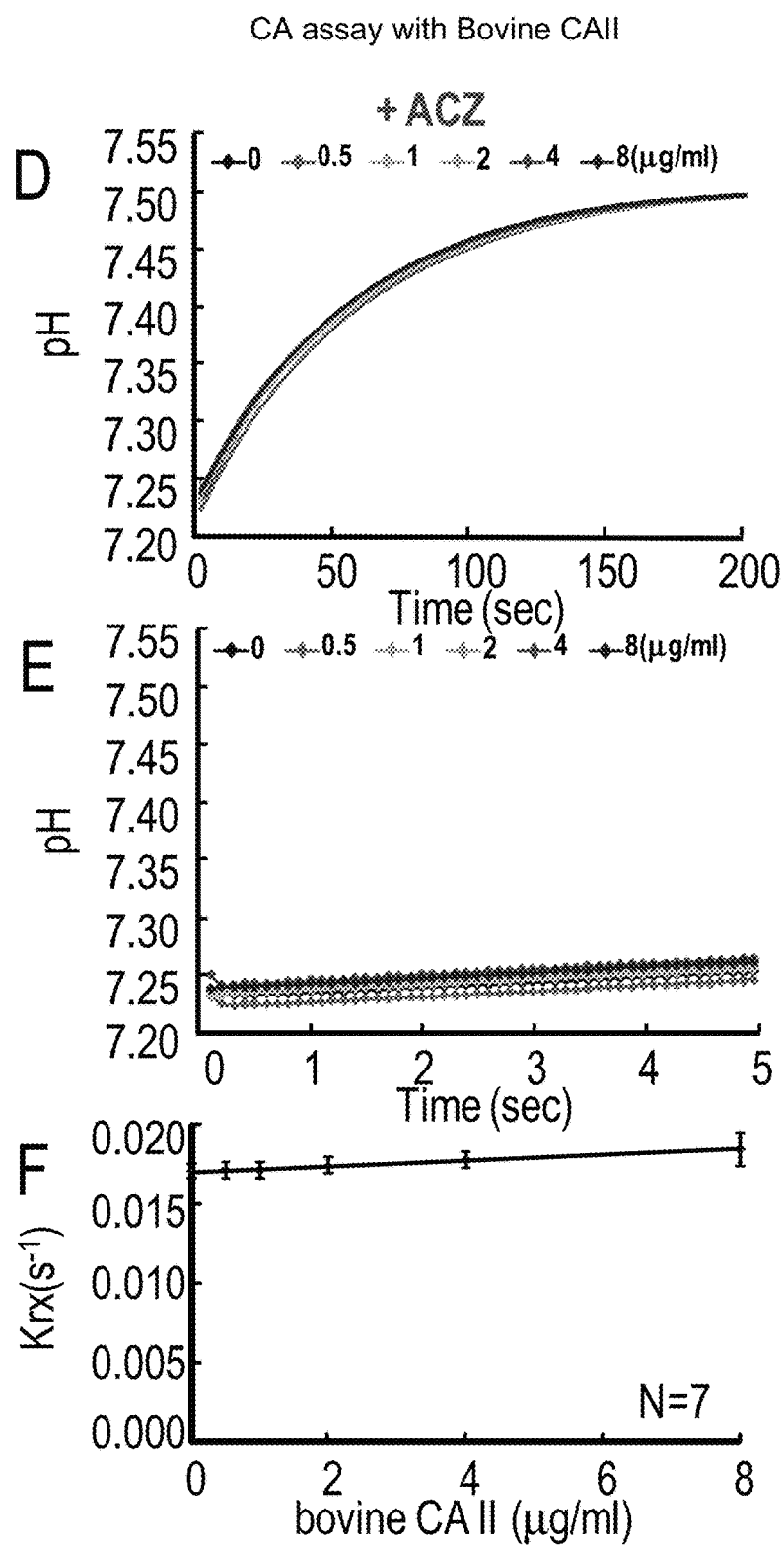
Figs. 2D-F

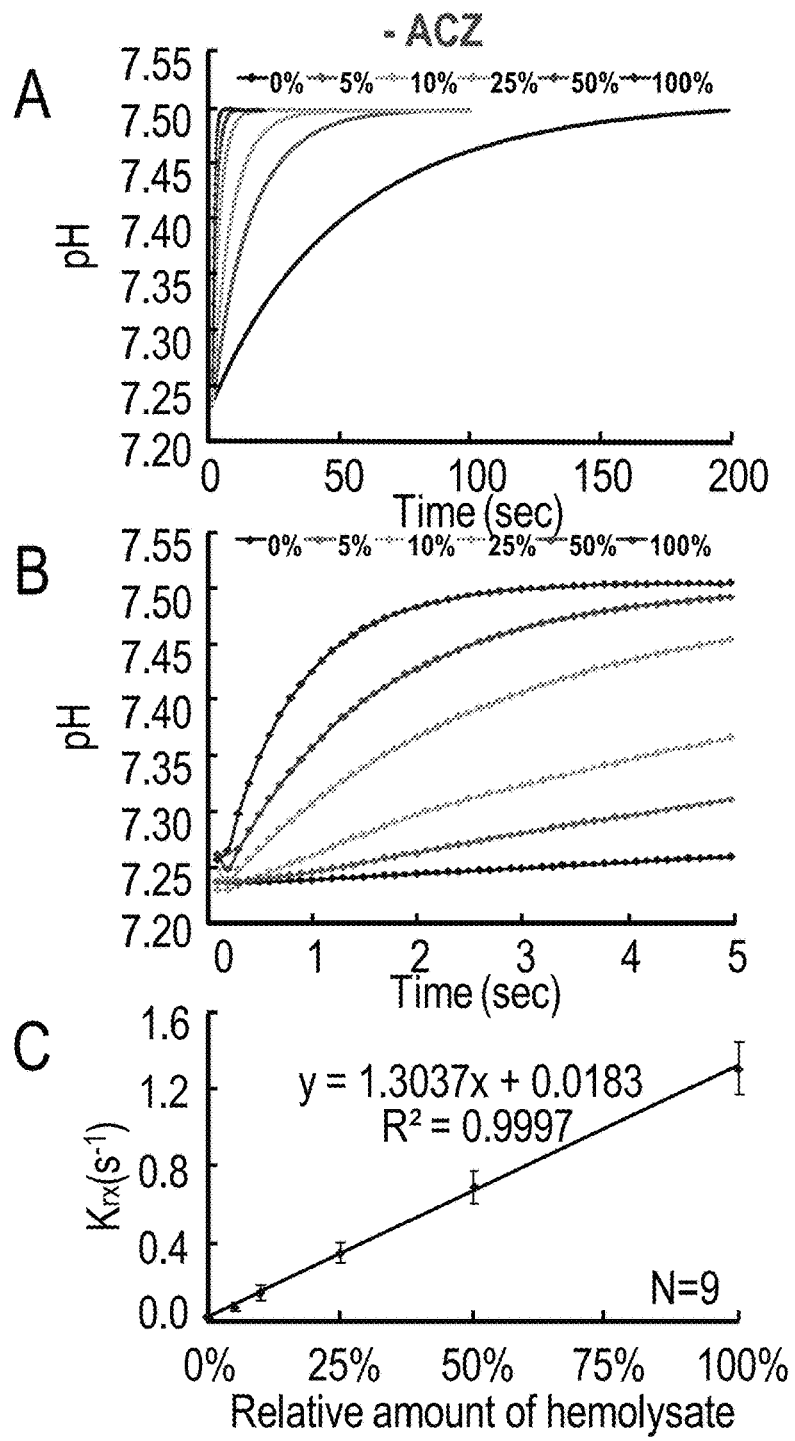
Figs. 3A-C

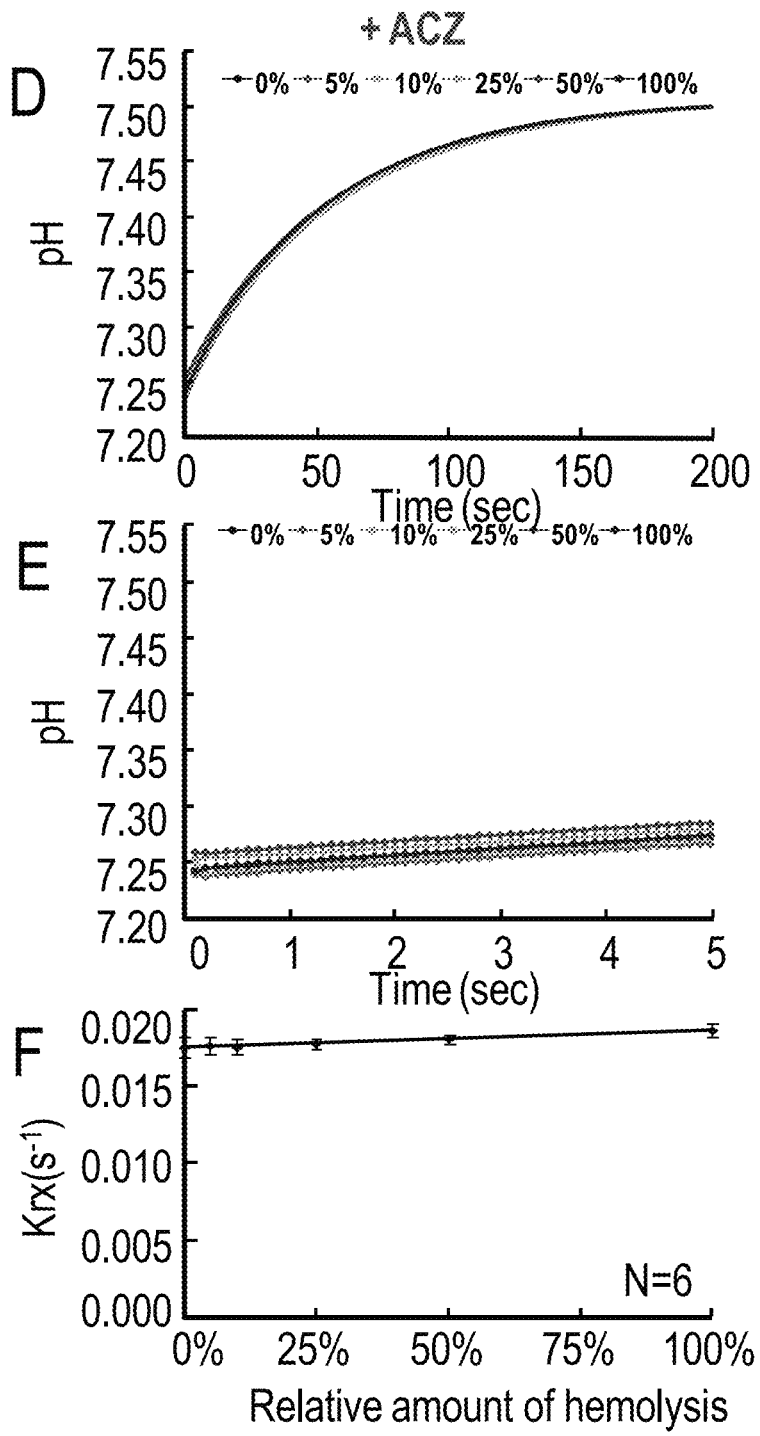
Figs. 3D-F

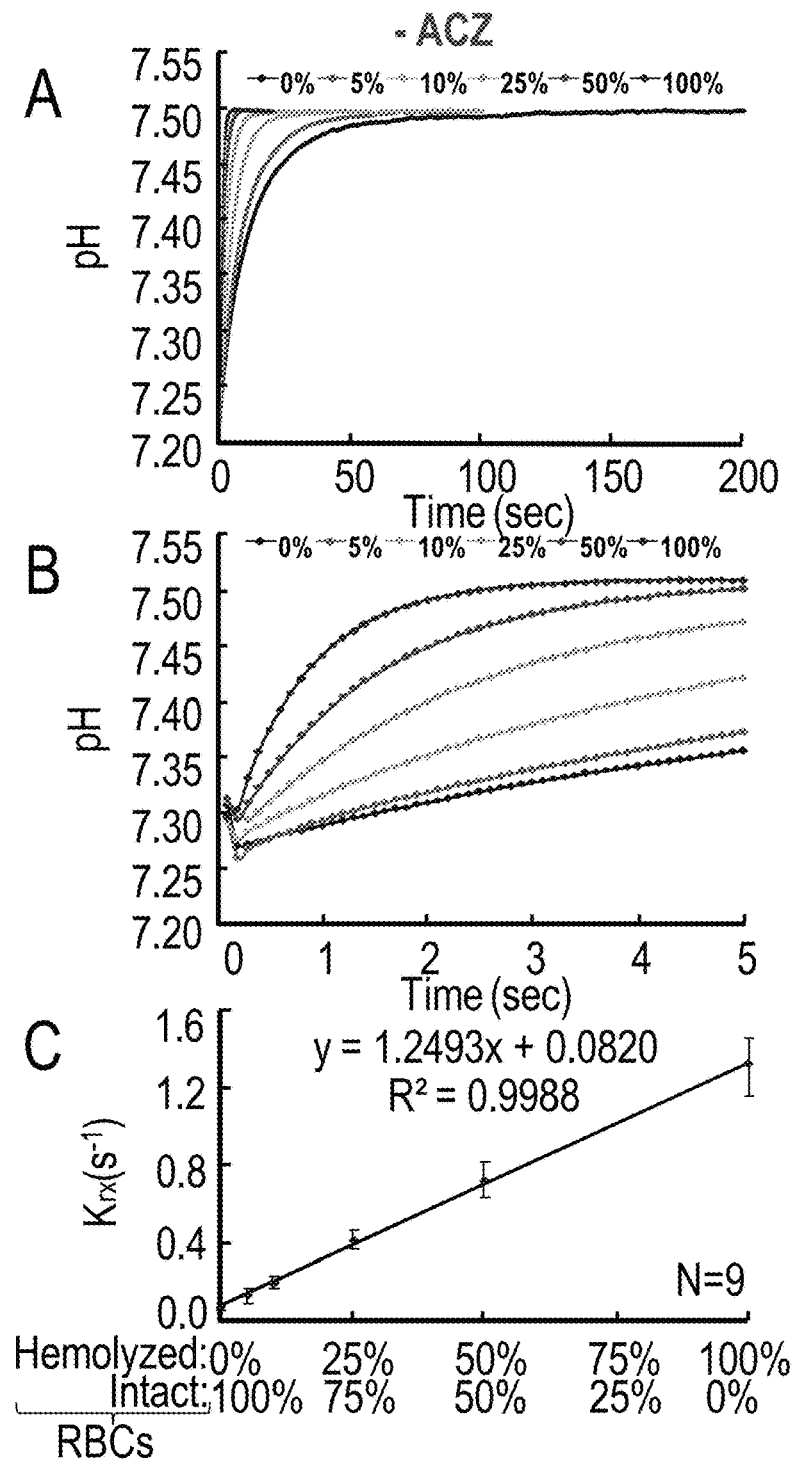
Figs. 4A-C

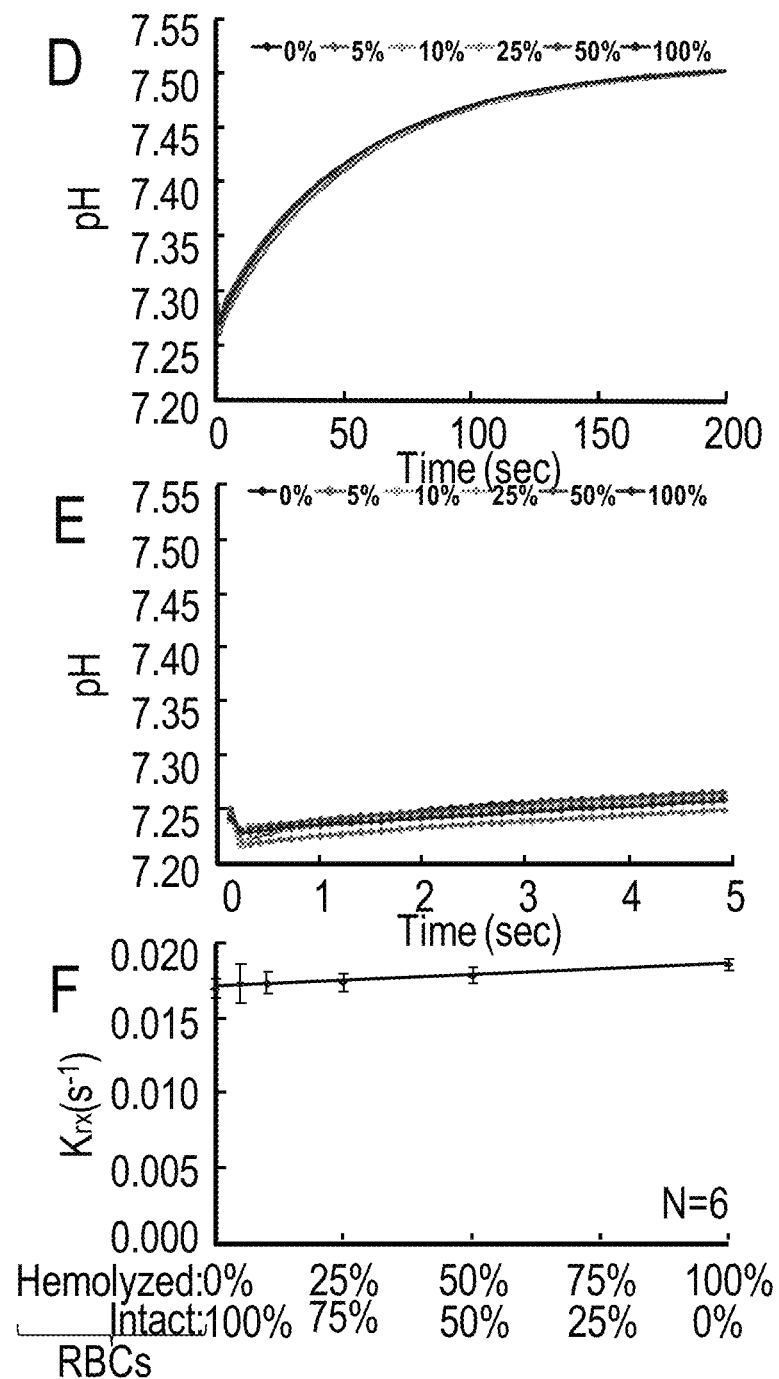
Figs. 4D-F

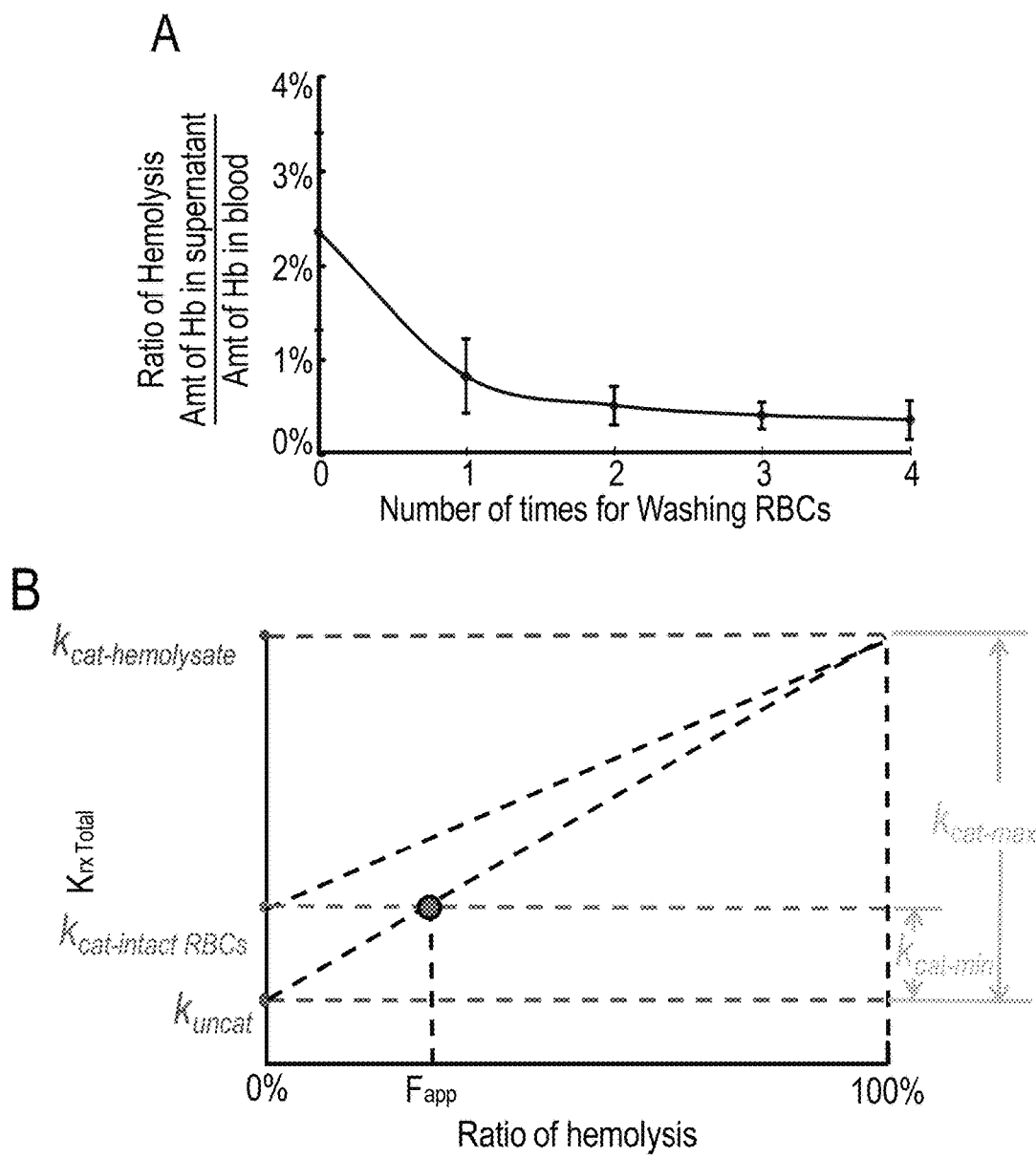
Figs. 5A-B

ASSAY AND METHOD FOR QUANTITATING CARBONIC ANHYDRASE ACTIVITY AND ASSESSING RED BLOOD HEMOLYSIS

RELATED APPLICATION

This application claims priority from U.S. Provisional Application No. 62/170,972, filed Jun. 4, 2015, the subject matter of which is incorporated herein by reference in its entirety.

GOVERNMENT FUNDING

This invention was made with government support under Grant Nos. N00014-08-1-0532, N00014-11-1-0889, N00014-09-1-0246, and N00014-12-1-0326 awarded by The Department of Defense—Office of Naval Research (ONR). The United States government has certain rights to the invention.

BACKGROUND

Carbonic anhydrase (CA) represents the second most abundant protein present inside erythrocytes. With the exception of the hagfish and other lampreys, carbonic anhydrase activity or content is normally extremely low in vertebrates in the plasma. Carbonic anhydrase exists in at least twelve different isozymes, with variable distribution among tissues. The CA-I and CA-II isozymes predominate in erythrocytes, with a small amount of CA-III. Isozymes CA-IV to XII are found in many other tissues, including the gut, kidney and lung. CA-IX is under study as a potential biomarker of renal and squamous cell carcinoma.

However, the characteristics and fate of free CA in plasma are poorly understood. Free CA-I, CA-II, and CA-III in plasma is rapidly bound and inactivated by a transferrin-like protein, followed by clearance in the reticuloendothelial system. Studies of radiolabelled CA in rats demonstrates an approximate half-life of two hours with elimination in the kidney and liver for CA isozymes I and II.

The activity of carbonic anhydrase can be measured by colorimetric assays, typically employing a substrate that is recognized and cleaved by the active site of CA. One such example is the compound para nitro phenylacetate. Since carbonic anhydrase has intrinsic esterase activity, it will cleave the dye (p-nitrophenol) from the acetate liberating a color in aqueous solution that can be assayed by standard colorimetric techniques. However, such a method has multiple limitations. First, the plasma of mammals contains other esterases that will hydrolyze the substrate molecule and liberate the dye (example given, acetyl cholinesterase), this enzyme assay liberates very non-specific results. Other problems with the enzymatic assay include the fact that CA is inhibited by circulating proteins, as well as drugs, including sulfanilimides, ethanol and morphine.

SUMMARY

Embodiments described herein relate to an assay for quantitating carbonic anhydrase activity and/or assessing red blood cell hemolysis in a bodily sample. The method and assay are based on mixing two dissimilar $CO_2/HCO_3^-$ solutions, and measuring the rate at which the pH of the newly mixed out of equilibrium solution equilibrates under the influence of the enzyme. The mixed out of equilibrium solutions undergo the reactions

causing pH of the mixed solution to rise. Because CA catalyzes the latter, otherwise slow reaction, the time course of pH or the rate of pH elibrium can be used to compute CA activity. Given the sensitivity, precision, and ease of the methodology, the assay and method described herein can be used in assessing red blood cell (RBC) fragility and RBC storage lesions before performing blood transfusions, and carbonic anhydrase release (and thus lysis) from a wide range of cells or tissues.

In some embodiments, the assay and methods described herein can be used in the detection of deterioration of stored blood, detection of problems with blood after cancer treatment, diagnosing anemia, diagnosing graft versus host disease (GVHD) after transplants, determining tissue viability for/during transplants, diagnosing/monitoring traumatic brain injury, shock, and/or concussions, and/or measuring blood toxicity and/or sepsis.

In some embodiments, the method can include mixing a bodily sample including red blood cells (RBC) and/or RBC lysate with a first physiological $CO_2/HCO_3^-$ solution. The first physiological $CO_2/HCO_3^-$ solution is then mixed with a second $CO_2/HCO_3^-$ solution having a dissimilar pH. The rate at which the pH of the newly mixed solution equilibrates under the influence of the carbonic anhydrase enzyme in the bodily sample is measured to determine carbonic anhydrase amounts and/or activity.

In some embodiments, an increase in the rate at which the pH of the newly mixed solution equilibrates compared to a control rate is indicative of an increase in enzyme or enzyme activity. In other embodiments, a decrease in the rate at which the pH of the newly mixed solution equilibrates compared to a control rate is indicative of a decrease in enzyme or enzyme activity.

In other embodiments, the first physiological $CO_2/HCO_3^-$ solution and the second $CO_2/HCO_3^-$ solution can be mixed in a stopped flow device by stop flow mixing. The rate at which the pH equilibrates can be measured by adding a fluorescent pH indicator dye to the first physiological $CO_2/HCO_3^-$ solution and/or the second physiological $CO_2/HCO_3^-$ solution and measuring a change of fluorescence of the dye upon mixing of the solutions. The fluorescent pH indicator dye can be pyranine. In one example, the pyranine dye can be provided in the first and/or second physiological $CO_2/HCO_3^-$ solution at a concentration of about 1 µM.

In some embodiments, the bodily sample includes red blood cells and/or red blood cell lysate from, for example, stored blood. An increase in determined enzyme or enzyme activity is indicative of increased red blood cell hemolysis; whereas a decrease in determined enzyme or enzyme activity is indicative of decreased red blood cell hemolysis.

In other embodiments, the first physiological $CO_2/HCO_3^-$ solution can be a 4-(2-hydroxyethyl)-1-piperazineethanesulfonic acid) (HEPES) buffered solution having a pH of about 7, and the second physiological $CO_2/HCO_3^-$ solution can have a pH of about 8.4 prior to mixing. The first physiological $CO_2/HCO_3^-$ solution and the second physiological $CO_2/HCO_3^-$ solution can have a temperature of about 10° C.

BRIEF DESCRIPTION OF THE DRAWINGS

FIGS. 2(A-F) illustrate plots showing the results of the carbonic anhydrase (CA) assay on purified bovine CAII (bCAII). A: Variation of pH with time (0~200 s) for different bCAII concentration (0~8 mg/ml). B: Variation of pH with time (0~5 s) for different bCAII concentration (0~8 mg/ml). C: Summary of data for ration between $k_{rx}$ and different BCAII concentration (0~8 mg/ml). bCA II was added into solution A, 2 mM pyranine was added into solution B (final concentration of 1 mM). Solution A and solution B was rapidly mixed at ratio 1:1 as described in method. pH variation vs. time curve was fitted by using least square method to get rate constant value $k_{rx}$. D: Variation of pH with time (0~200 s) for role of CA inhibitor ACZ on different bCAII concentration (0~8 mg/ml). E: Variation of pH with time (0~5 s) for role of CA inhibitor ACZ on different bCAII concentration (0~8 mg/ml). F: Summary of data for ration between $k_{rx}$ and role of CA inhibitor ACZ on different bCAII concentration (0~8 mg/ml). bCA II was added into solution A, 20 µM ACZ and 2 mM pyranine were added into solution B. Solution A and solution B was rapidly mixed at ratio 1:1 as described in method. pH variation vs. time curve was fitted by using least square method to get rate constant value $k_{rx}$.

FIGS. 3(A-F) illustrate plots showing the results of the carbonic anhydrase (CA) assay on mouse hemolysate. A: Variation of pH with time (0~200 s) for relative amount of hemolysate. B: Variation of pH with time (0~5 s) for relative amount of hemolysate. C: Summary of data for ration between $k_{rx}$ and relative amount of hemolysate. Hemolysate was added into solution A, 2 mM pyranine was added into solution B. Solution A and solution B was rapidly mixed at ratio 1:1 as described in method. pH variation vs. time curve was fitted by using least square method to get rate constant value $k_{rx}$. D: Variation of pH with time (0~200 s) for role of CA inhibitor ACZ on relative amount of hemolysate. E: Variation of pH with time (0~5 s) for role of CA inhibitor ACZ on relative amount of hemolysate. F: Summary of data for ration between $k_{rx}$ and role of CA inhibitor ACZ on relative amount of hemolysate. Hemolysate was added into solution A, 10 µM ACZ and 2 mM pyranine were added into solution B. Solution A and solution B was rapidly mixed at ratio 1:1 as described in method. pH variation vs. time curve was fitted by using least square method to get rate constant value $k_{rx}$.

FIGS. 4(A-F) illustrate plots showing the results of the carbonic anhydrase (CA) assay on mixtures of intact and hemolyzed RBCs. A: Variation of pH with time (0~5 s) for varying hemolysis of RBCs. B: Variation of pH with time (0~200 s) for varying hemolysis of RBCs. C: Summary of data for ration between $k_{rx}$ and varying hemolysis of RBCs. RBCs were added into solution A, 2 mM pyranine was added into solution B. Solution A and solution B was rapidly mixed at ratio 1:1 as described in method. pH variation vs. time curve was fitted by using least square method to get rate constant value $k_{rx}$. D: Variation of pH with time (0~200 s) for role of CA inhibitor ACZ on varying hemolysis of RBCs. E: Variation of pH with time (0~5 s) for role of CA inhibitor ACZ on varying hemolysis of RBCs. F: Summary of data for ration between $k_{rx}$ and role of CA inhibitor ACZ on varying hemolysis of RBCs. RBCs were added into solution A, 10 µM ACZ and 2 mM pyranine were added into solution B. Solution A and solution B was rapidly mixed at ratio 1:1 as described in method. pH variation vs. time curve was fitted by using least square method to get rate constant value $k_{rx}$.

DETAILED DESCRIPTION

Figure 1:
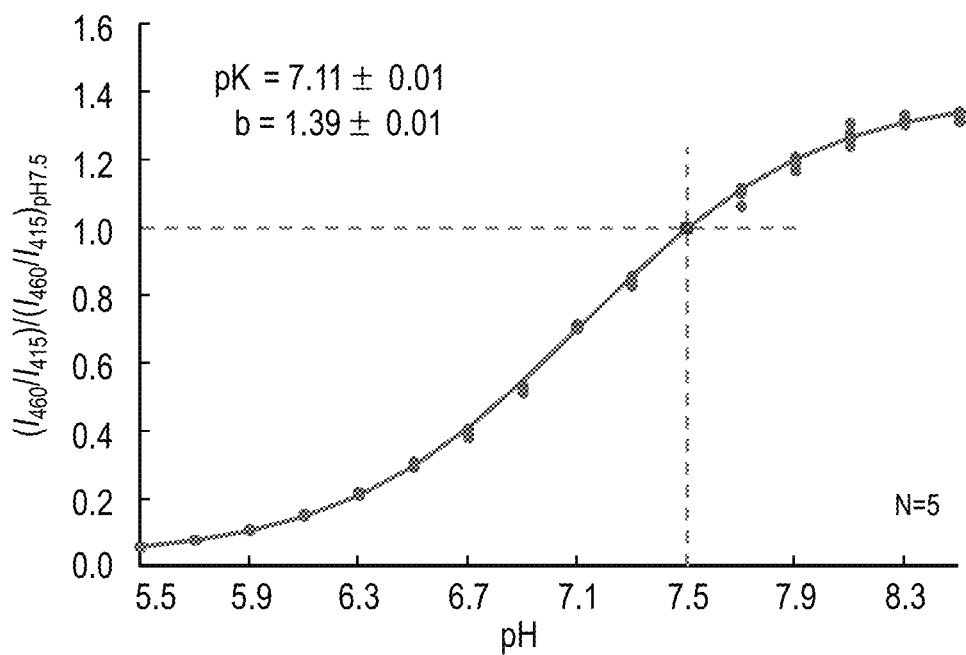
FIG. 1 illustrates a plot showing dependence of normalized fluorescence-excitation ratio on pH. For each pH, fluorescence spectra were recorded at either excited wavelength 460 nm ($I_{460}$) or 415 nm ($I_{415}$). After subtracting the background value of each excitation wavelength ($I_{o460}$ and $I_{o415}$), ($I_{460}-I_{o460}$ and $I_{415}-I_{o415}$) value at each pH were calculated. We obtained the best-fit curve, which is forced to pass through a value of 1.0, at a pH of 7.5. The data are from five sets of experiments.

Embodiments described herein relate to a method of measuring the activity of carbonic anhydrase enzymes with high precision and high time resolution. The method is based on mixing two dissimilar $CO_2/HCO_3^-$ solutions, and measuring the rate at which the pH of the newly mixed solution equilibrates under the influence of the enzyme. Advantageously, the method described herein employs a physiological $CO_2/HCO_3^-$ solution, and after mixing with the second $CO_2/HCO_3^-$ solution, the mixture is very close to being physiological. Thus, one can deliver and assay the enzyme under physiological conditions, which is impossible using the previous methodologies.

In some embodiments, the assay and method described herein can be used in the assessment of hemolysis (the breaking open of red blood cells, RBCs), which results in the release of carbonic anhydrase enzyme from the cells. In other embodiments, the assay and method described herein can be used to measure RBC fragility.

The percentage of hemolysis is used to diagnose and monitor diseases and conditions that produce intravascular hemolysis as well as to optimize the therapeutic efficacy of treatment for hemolysis. Carbonic anhydrase, exists in high concentrations in erythrocytes, but not in plasma. It was determined that the method described herein uses the CA present in plasma as a quantitative biological indicator of intravascular hemolysis.

The significance of a test to quantify the percentage of hemolysis in a sample would have applicability to many diseases. These include genetic hemoglobinopathies, inherited abnormalities of the erythrocyte, including spherocytosis, paroxysmal nocturnal hemoglobinuria, thalassemias, disseminated intravascular coagulation secondary to infection, trauma, or cancer, erythrocyte destruction secondary to immune response to drugs, viral infections, and other stimuli, erythrocyte destruction secondary intravascular devices such as heart valves or from pulmonary hypertension.

Additionally, the assay and methods described herein can be used in the detection of deterioration of stored blood, detection of problems with blood after cancer treatment, diagnosing anemia, diagnosing graft versus host disease (GVHD) after transplants, determining tissue viability for/during transplants, diagnosing/monitoring traumatic brain injury, shock, and/or concussions, and/or measuring blood toxicity and/or sepsis.

In some embodiments, the method can include mixing a bodily sample including red blood cells (RBC) and/or RBC lysate with a first physiological $CO_2/HCO_3^-$ solution. The first physiological $CO_2/HCO_3^-$ solution is then mixed with a second $CO_2/HCO_3^-$ solution having a dissimilar pH. The rate at which the pH of the newly mixed solution equilibrates under the influence of the enzyme is measured to determine carbonic anhydrase amounts and/or activity.

In some embodiments, an increase in the rate at which the pH of the newly mixed solution equilibrates compared to a control rate is indicative of an increase in enzyme or enzyme activity. In other embodiments, a decrease in the rate at which the pH of the newly mixed solution equilibrates compared to a control rate is indicative of a decrease in enzyme or enzyme activity. The control rate can be a predetermined value or control value based upon the rate at which the pH equilibrates in comparable solutions having no carbonic anhydrase or fixed or defined levels of carbonic anhydrase.

The first physiological $CO_2/HCO_3^-$ solution and the second $CO_2/HCO_3^-$ solution can be mixed in a stopped flow device by stop flow mixing. Stopped-flow mixing techniques, have been widely used to induce rapid changes in concentration and trigger chemical reactions, thus getting real time information. These techniques use a reactor to rapidly mix together solutions, which then flow into an observation cell. A stop syringe is used to limit the volume of solution within the cell by abruptly stopping the flow. The product is then analyzed using optical properties and techniques (absorbance, fluorescence, light scattering, spectroscopic technique, etc.). The measurement of these optical properties is performed by system detectors which can be mounted either perpendicular or parallel to the path of incoming light. The time resolution is often of the order of milliseconds or lower.

In some embodiments, the rate at which the pH equilibrates can be measured by adding a fluorescent pH indicator dye to the first physiological $CO_2/HCO_3^-$ solution and/or the second physiological $CO_2/HCO_3^-$ solution and measuring a change of fluorescence of the dye upon mixing of the solutions. The fluorescent pH indicator dye can be pyranine. The pyranine dye can be provided in the first and/or second physiological $CO_2/HCO_3^-$ solution at concentration of about 1 μM.

In some embodiments, the bodily sample includes red blood cells and/or red blood cell lysate from, for example, stored blood. An increase in determined enzyme or enzyme activity is indicative of increased red blood cell hemolysis; whereas a decrease in determined enzyme or enzyme activity is indicative of decreased red blood cell hemolysis.

In other embodiments, the first physiological $CO_2/HCO_3^-$ solution can be a 4-(2-hydroxyethyl)-1-piperazineethanesulfonic acid) (HEPES) buffered solution having a pH of about 7 and the second physiological $CO_2/HCO_3^-$ solution having a pH of about 8.4 prior to mixing. The first physiological $CO_2/HCO_3^-$ solution and the second physiological $CO_2/HCO_3^-$ solution having a temperature of about 10° C.

Other embodiments relate to a test or kit for the detection of hemolysis up to about 10%. This is a very important range clinically because, for example, at concentrations such as 8 to 10% the plasma begins to turn pink which is a visible indicator of free hemoglobin. The test or kit of the present invention is useful to identify patients with chronic diseases who are susceptible to hemolysis, and possibly to discover it earlier. For example, the test or kit could be used for various medical applications including, but not limited to, monitor patients on drugs that predispose to hemolysis as well as patients with hemoglobinopathies, patients at risk for disseminated intravascular coagulation, monitor malaria, assess severity of pulmonary hypertension, and for the initial work-up for anemia.

Further embodiments relate to a method of diagnosing or treating a patient. The method comprises obtaining a percentage of hemolysis from a nomogram comprising a first set of data corresponding to optical density of a plasma component of a blood sample obtained from a subject and a second set of data corresponding to carbonic anhydrase I activity. The first set of data and the second set of data are plotted to form a graphical measure or an equation used to determine the percentage of hemolysis in the sample. The obtained percentage of hemolysis is used to diagnose or to treat the patient. For example, in the case of treatment by dosage of medication, a value of 0% hemolysis indicates a zero dosage amount, a value above 5% hemolysis indicates full dosage, and a value between 0 and 5% hemolysis indicate partial dosage, determined in proportion to the percentage of hemolysis obtained.

EXAMPLE

In this Example, we describe novel methods for assaying carbonic anhydrase (CA) activity in a stop flow (SF) device, and then extending this assay to assess red blood cell (RBC) hemolysis. The CA assay uses out-of-equilibrium (OOE) $CO_2/HCO_3^-$ solutions with combinations of $[CO_2]$, $[HCO_3^-]$, and pH. In particular, two dissimilar $CO_2/HCO_3^-$ solutions—(A) 0% $CO_2$/0 $HCO_3^-$/pH 7.03 and (B) 1% $CO_2$/44 mM $HCO_3^-$/pH 8.41 are mixed to create in a reaction cell of a SF device a designated initial OOE state, e.g., 0.5% $CO_2$/22 mM $HCO_3^-$/pH 7.2, where the pH is far too low for the designated $[CO_2]/[HCO_3^-]$ ratio. Thus, the system spontaneously undergoes the reactions

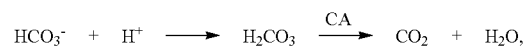

causing pH in the SF cell to rise to 7.50. Because CA catalyzes the latter, otherwise slow reaction, the time course of pH, reported by the fluorescent dye pyranine, can be used to compute CA activity. We validated this technique on purified bovine CA II and hemolysates of mouse blood, and then applied it to intact murine RBCs. Given the sensitivity, precision, and ease of our methodology, this approach is valuable for assessing RBC fragility RBC storage lesions before performing blood transfusions, and CA release (and thus lysis) from a wide range of cells or tissues.

Materials and Methods

Solutions

The compositions of solutions are shown in (Table 1). For the CA assay, we mixed solution A with solution B in the SF device to obtain the initial OOE soluition ("Mix") in the reaction cell. To achieve the desired pH, we titrated solutions with NaOH or HCl either at room temperature (RT, for RBC washing solution) or at 10° C. (for pH calibration solution and OOE A and B solutions). pH measurements were recorded on a portable pH meter (model A121 Orion Star, Thermo Scientific, Beverly, Mass.) fitted with a pH electrode (Ross Sure-Flow combination pH Electrode, Thermo Scientific) at RT or at 10° C. For all work at 10° C., both pH titration of solutions and the actual experiments, we used a refrigerated, constant temperature, shaker waterbath (model RWB 3220, Thermo Fisher Scientific Inc., Asheville, N.C.) and several telesystem magnetic stirrers (Thermo Fisher Scientific). Beakers containing the pH calibration buffers (pH at 6, 8 and 10, Fisher Scientific, Fair Lawn, N.J.), the solutions to be titrated, and the pH electrode were equilibrated at either RT or 10° C. Osmolality was measured using a vapor pressure osmometer (Vapro 5520; Wescor, Inc., Logan, Utah), and adjusted upward if necessary by the addition of NaCl.

TABLE 1

Physiological solutions

| Component or parameter | RBC washing solution | pH calibration solution for dye | OOE Solution for CA assay | | |
|---|---|---|---|---|---|
| | | | A | B | Mix¶ |
| NaCl (mM)* | 92.5 | 150 | 140 | 116 | 128 |
| KCl (mM) | 0 | 3 | 3 | 3 | 3 |
| CaCl$_2$ (mM) | 0.01 | 1 | 2 | 0 | 1 |
| Na$_2$HPO$_4$ (mM)* | 46.98 | 0 | 0 | 0 | 0 |
| NaH$_2$PO$_4$ (mM)* | 11.02 | 0 | 0 | 0 | 0 |
| HEPES (mM)† | 0 | 8 | 16 | 0 | 8 |
| NaHCO$_3$ (mM)‡ | 0 | 0 | ~0 | 44 | 22 |
| CO$_2$ (%) | 0 | 0 | ~0 | ~1 | 0.5 |
| pH | ~7.40* | 7.50† | 7.03† | 8.41‡ | ~7.25 |
| Pyranine (μM)§ | 0 | 1 or 0 | 0 | 2 or 0 | 1 or 0 |
| Sample of CA, lysate, or RBCs | 0 | 0 | ++ | 0 | + |
| Temperature (° C.) | RT | 10 | 10 | 10 | 10 |
| Osmolality | ~300 | ~295 | ~295 | ~300 | ~298 |

*The ratio [HPO$_4^-$]/[H$_2$PO$_4^-$] determined the final pH at RT room temperature (RT, ~22° C.).
†We titrated HEPES free acid (pK ~7.5) to pH 7.50 with NaOH, and then in some aliquots added either HCl or more NaOH to achieve pH values from 5.50 to 8.30 at 10° C. After the titration, we added HPTS to equal concentrations in each solution.
‡The addition of HCO$_3^-$ generates some CO$_2$ and CO$_3^=$; this mixture determined the final pH at 10° C.
§[Pyranine] was present at a final concentration of 1 μM (to obtain pH data) or 0 μM (to obtain background data).
¶The values in this column are those at the instant of mixing solutions A and B. The solution is out of equilibrium because the pH of 7.25 is far too low, given [HCO$_3^-$] = 22 mM and CO$_2$ = 0.5%.

Stopped-Flow Fluorescence Spectroscopy

Rapid mixing of solutions A and B was performed using the SX-20 stopped-flow apparatus (Applied Photophysics, Leatherhead, UK). We excited the pH-sensitive fluorescent dye pyranine using an excitation wavelength of 460 nm (pH-sensitive wavelength), and or of 415 nm (pH-independent isosbestic point) while monitoring total fluorescence emission using a 488-nm cut-off filter. The sampling period of the SF device was 12.5 μs. Because the output of the device was 1 data point every 0.1 s, each data point represents $(10^{-1}$ s$)/(12.5 \times 10^{-6}$ s$)=8000$ samples. Our duration of data collection ranged from 20 s (i.e., 200 data points) for rapid reactions (i.e., high CA activity) to 200 s (i.e., 2000 data points) for slow reactions (e.g., the uncatalyzed reaction).

For each experimental sample, we acquired two time courses in the presence of dye (Table 1), a time course of $I_{Total,460}$ during one stopped-flow shot while exciting at 460 nm, and then a time course of $I_{Total,415}$ during a second shot while exciting at 415 nm. Also for each experimental sample, we acquired two time courses in the absence of dye (Table 1), $I_{Background,460}$ and $I_{Background,415}$.

After correcting for background, we obtained for each experimental sample the time course of the ratio $(I_{460}/I_{415})=[(I_{Total,460}-I_{Background,460})/(I_{Total,415}-I_{Background,415})]$, which we converted to the time course of pH as described below.

Calibration of Dye

We calibrated the pH indicator dye pyranine at 10° C. by mixing in the SF device two identical solutions that were either the pH-7.50 "pH calibration solution for dye" listed in (Table 1), or variants thereof obtained by titrating the pH as outlined in a footnote to (Table 1). For each pH value X, we computed $(I_{460}/I_{415})_{pHx}$ as described in the previous section. We fitted the following theoretical titration curve to our experimental data:

$$\frac{(I_{460}/I_{415})_{pHx}}{(I_{460}/I_{415})_{pH\,7.5}} = 1 + b\left[\frac{10^{(pH\,x-pK)}}{1+10^{(pH\,x-pK)}} - \frac{10^{(7.5-pK)}}{1+10^{(7.5-pK)}}\right],$$

which normalizes the data to the value observed at pH 7.5, and forces the function to have a value of unity at this pH.

We used an iterative non-linear least-squares method to determine b and pK. FIG. 1 shows a plot of the data from five sets of experiments, as well as the best-fit curve. The best-fit values were 7.11±0.01 (SD) for the pK, and 1.39±0.01(SD) for b. We used these values of pK and b and the values for ratio of $(I_{460}/I_{415})$ in each experiment to calculate pH.

Carbonic Anhydrase (CA) Assay

For some experiments, we obtained purified bovine carbonic anhydrase II (bCAII), isolated from erythrocytes (C2522, Sigma-Aldrich, St. Louis, Mo.), and resuspended it in 0.2% bovine serum albumin at a concentration of 1 mg/mL. We added varying amounts of bCAII to establish concentrations from 0.5 to 8 μg/mL in solution A (Table 1). Rapid mixing with solution B (containing 2 μM pyranine) at 10° C. in the SF reaction cell initiates the reactions

$$HCO_3^- + H^+ \longrightarrow H_2CO_3 \xrightarrow{CA} CO_2 + H_2O,$$

causing pH to rise exponentially. Under stopped-flow conditions, we exploited the fluorescence of pyranine to monitor this pH trajectory as described above. In other experiments, instead of adding bCAII to solution A, we added murine RBC lysate (described below), murine RBCs (described below), or mixtures of the two.

We fitted the pH time course with the equation:

$$pH(t) = A - Be^{-kt},$$

where t is time, A is the final (equilibrated) value of pH, B is the pH range, and k is the rate constant. We obtained A, B, and k using least square method.

Blood Collection

Adult C57/BL6 mice (8 to 16 weeks old) were sacrificed by cervical dislocation and blood was immediately collected by cardiac puncture using a 1-mL syringe (Becton, Dickinson and Co., Franklin Lakes, N.J., USA) with a 23 gauge PrecisionGlide needle (Becton, Dickinson and Co.). Prior to blood collection the syringe and needle were rinsed with 0.9% sodium heparin (H4784, Sigma-Aldrich). The blood was transferred to a 1.5-mL microcentrifuge tube, centrifuged in a Beckman Microfuge 16 Microcentrifuge (Beckman, Brea, Calif.) at 600×g for 10 min and the resulting supernatant and buffy coat were removed. To remove any residual extracellular Hb, the pelleted red blood cells (RBCs) were resuspended—in solution A to a 10% hematocrit (Hct)—and centrifuged at 600×g for 5 minutes. This process was repeated 4×. After the final wash the RBCs were resuspended in solution A to a final Hct of ~20% to ~30%.

We computed The Hb concentration using a novel least-square's approach, based on Beer's law (see Appendix). C is generally calculated by C [Hb]=$A_\lambda/l\varepsilon_\lambda$, where $A_\lambda$ is absorbance at wavelength λ, l is pathlength (cm) and $\varepsilon_\lambda$ is the molar extinction coefficient in (cm$^{-1}$ M$^{-1}$). Absorbances at 560 nm ($A_{560}$), 576 nm ($A_{576}$), and 650 nm ($A_{650}$) were determined based on visible absorbance spectroscopy on a Beckman Coulter 730 Life science UV/Vis Spectrophotometer (Beckman, Brea, Calif.), using a pathlength (l) of 1 cm. The calculation requires the molar extinction coefficients, from which we obtained $A_{560}$ the absorbance at (560 nm is ($A_{560}$, a local valley for oxygenated Hb), $A_{576}$ (576 nm is ($A_{576}$, a local peak), and $A_{650}$ (650 nm is ($A_{650}$, a background value. $\varepsilon_{560}=32{,}613.2$ cm$^{-1}$ M$^{-1}$ and $\varepsilon_{576}=55{,}540$ cm$^{-1}$ M$^{-1}$: together with $A_{560}$ and $A_{576}$ were then used to match the equation to determine C by least square method, which lead to The following equation $$C = \frac{(A_{560} - A_{650})^2 + (A_{576} - A_{650})^2}{L?(A_{560} - A_{650})\varepsilon_{560} + L?(A_{576} - A_{650})\varepsilon_{576}}$$

$$[Hb](M) = \frac{\frac{(A_{560} - A_{650})}{\ell \varepsilon_{560}} + \frac{(A_{576} - A_{650})}{\ell \varepsilon_{576}}}{2}$$

$$[Hb](M) = \frac{\frac{(A_{560} - A_{650})}{\ell \varepsilon_{560}} + \frac{(A_{576} - A_{650})}{\ell \varepsilon_{576}}}{2} = \frac{\frac{A_{560} \text{ (dimensionless)}}{(1 \text{ cm})(32{,}613 \text{ cm}^{-1}\text{M}^{-1})} + \frac{A_{576}}{\ell \varepsilon_{576}}}{2},$$

The RBCs were maintained for up to ~5 h on ice at the Hct used for the [Hb] determination for experiments performed that day.

Simulated Hemolysis

A solution of isolated Hb was obtained by osmotic lysis of 20 μL of freshly prepared mouse RBCs (see above) in pure $H_2O$ (1:8 dilution), followed by centrifugation at 15000×g for 5 minutes in a Beckman Microfuge 16 Microcentrifuge, at RT room temperature. This centrifugation step separated the cellular debris from the Hb containing supernatant. The supernatant (cleared of cellular debris) then was removed and transferred to a clean 1.5 mL Eppendorf tube for a The Hb concentration of the supernatant was spectroscopic determination of [Hb] using the visible absorbance spectroscopy as described above.

In experiments in which we determined the effect of hemolysate on the rate constant of the $H_2CO_3$ dehydration reaction, we diluted lysate supernatant (see previous paragraph) into OOE solution A (Table 1), at a dilution of ~1:200 to ~1:2000 he relative amount of hemolysis was generated from only hemolysates by replacing the proportion of intact RBCs with same volume of solution A.

Simulated degrees of hemolysis (0-up to 100%) were achieved by mixing different proportions of freshly prepared, ostensibly "intact" RBCs and a lysate (representing 100% lysis), while maintaining the total Hb concentration at 5 μM (Table 2). For example, the mixture simulating ostensibly 0% hemolysis contained 5 μM Hb from RBCs. The mixture simulating ostensibly 50% hemolysis contained 2.5 μM Hb from RBCs and 2.5 μM Hb from the lysate supernatant (added to the RBC mixture in a dilution of ~1:400 to ~1:4000, depending on the [Hb]). The 100% hemolysis solution contained 5 μM Hb from the lysate supernatant (diluted into OOE solution A, (Table 1). We similarly generated other variations of simulated hemolysis were assembled accordingly. The relative amount of hemolysis was generated from only hemolysates by replacing the proportion of intact RBCs with same volume of solution A.

TABLE 2

Establishing the fraction of apparent hemolysis

| % Apparent hemolysis | Intact RBCs* | RBC hemolysate* |
|---|---|---|
| 0% | 100% | 0% |
| 5% | 95% | 5% |
| 10% | 90% | 10% |
| 25% | 75% | 25% |
| 50% | 50% | 50% |
| 100% | 0% | 100% |

*100% refers to 5 μM hemoglobin

Analysis of Data

Data were analyzed with two-tailed unpaired student's test. Results are shown as mean±SD.

Results

CA Assay on Purified Bovine CA II

We developed a novel assay for CA, based on the use of out-of-equilibrium (OOE) $CO_2/HCO_3^-$ solutions in a stopped-flow device. OOE technology makes it possible to generate, for a brief period of time, solutions in which $CO_2$, $HCO_3^-$, and pH can be far out of equilibrium. For the conditions we chose, $pH_o$ at the instant of mixing is approximately 7.25. Over the ensuing seconds, the reaction $HCO_3^- + H^+ \rightarrow CO_2 + H_2O$ causes $pH_o$ to rise to about 7.50 (FIG. 2 FIGS. 2A & 2B). With no added CA (0 μg/ml), $pH_o$ rises very slowly, reaching about 7.50 in ~200 s (FIG. 2A). It clearly showed that adding incremental amounts of commercially available purified bCAII greatly speeds the equilibration of $pH_o$ (0.5, 1, 2, 4, and 8 μg/ml in FIG. 2B). For each [bCAII], the rate constant of the reaction was calculated, by using least square approach to fit each curve in FIG. 2A. FIG. 2C summarizes the dependence of $k_{rx}$ on [bCAII]. Adding purified bovine CAII substantially increases $k_{rx}$ in a [CA]-dependent fashion. Note that this dependence is linear, with a y-intercept of ~0.0185 s$^{-1}$, which is the rate constant of the uncatalyzed reaction. We next studied the role of CA blocker acetazolamide (ACZ) on bCAII enzyme activity. 20 μM ACZ was added in the syringe opposite to the bCAII. In FIGS. 2D & 2E, as expected, ACZ significantly blocked bCAII (0.5-8 μg/ml) catalyzed $HCO_3^- + H^+ \rightarrow CO_2 + H_2O$ reaction, which reduced $k_{rx}$ to the uncatalyzed value (~0.02 s$^{-1}$) (FIG. 2F).

CA Assay on Mouse Hemolysate

We next began to work with murine RBCs to determine if CA assay can quantitate hemolysis. FIG. 3A shows six pH trajectories, similar to the ones in FIG. 2A except that here (FIG. 3A) we replaced bCAII with lysate from wt mouse RBCs. "100%" is the hemolysate from all RBCs (final HCT≅0.15%) including of 5 μM hemoglobin; "50%" is half this amount of hemolysate, etc. Without RBC lysate (in FIGS. 3A & 3B), $pH_o$ rises very slowly from around 7.25 to reach ~7.50 in ~200 s (FIG. 3A). It clearly showed that adding incremental amounts of hemolysate greatly speeds the equilibration of $pH_o$ (relative amount of 5%, 10%, 25%, 50%, and 100% hemoglobin in FIG. 3B). FIG. 3C summarizes these data (each N=blood from 1 mouse). As expected, this dependence is linear, with a y-intercept of ~0.0183 s$^{-1}$, which is very close to the rate constant of the uncatalyzed reaction in FIG. 2C. We next studied the role of CA blocker acetazolamide (ACZ) on hemolysate released CA enzyme activity. 10 μM ACZ was added in the syringe opposite to the hemolysate. In FIGS. 3D and 3E, similar to the case with bCAII, ACZ significantly blocked hemolysate released CA (5%~100% relative amount of hemolysate) catalyzed $HCO_3^- + H^+ \rightarrow CO_2 + H_2O$ reaction, which reduced $k_{rx}$ to the uncatalyzed value (~0.02 s$^{-1}$) (FIG. 3F).

CA Assay on Mixtures of Intact and Hemolyzed Mouse RBCs

We mixed in different proportions of (a) freshly prepared, ostensibly "intact" RBCs (≅0.3% HCT) with (b) a lysate from an equivalent mass of RBCs. The total [Hb] constant was kept at 5 μM (the amount in a 0.15% HCT) to simulate degrees of hemolysis (0-100%). FIG. 4B shows six pH trajectories in five sec, it is clearly showed that the higher ratio of simulate hemolysis of RBCs, the more CA released, and the faster of speed to get the equilibration of $pH_o$ for this CA catalyzed reaction. In FIG. 4A, it showed that 50% and 100% hemolysis of RBCs (total amount of 5 μM hemoglobin) released much more CA that greatly speeds the reaction $HCO_3^- + H^+ \rightarrow CO_2 + H_2O$ to equilibrium in 10 seconds. Though 0% hemolysis of intact RBCs speeds the reaction to equilibrium is in 100 sec, it is still faster than uncatalyzed reaction rate (in 200 sec of FIGS. 2A and 3A). FIG. 4C summarizes the results of FIG. 4A. The $k_{rx}$ vs. % hemolysis relationship is still linear. In FIG. 4C, y-intercept of ~0.0820 s$^{-1}$ is the rate constant of RBCs from wt mice (≅0.3% HCT), which is higher than that in FIG. 2C or 3C, indicating that even seemingly intact wt RBCs are partially hemolyzed in the SF cell. We next studied the role of CA blocker acetazolamide (ACZ) on intact RBCs and hemolysate released CA enzyme activity. 10 μM ACZ was added in the syringe opposite to the RBCs. In FIG. 4D or 4E, similar to the case with bCAII (FIG. 2D or 2E) and mouse hemolysate (FIG. 3D or 3E), ACZ significantly blocked intact RBCs and hemolysate released CA (5%~100% hemolysis of RBCs) catalyzed $HCO_3^- + H^+ \rightarrow CO_2 + H_2O$ reaction, which reduced $k_{rx}$ to the uncatalyzed value (~0.02 s$^{-1}$) (FIG. 4F). This ACZ result means that these extracellular CA that released from RBCs catalyzed the reaction $HCO_3^- + H^+ \rightarrow CO_2 + H_2O$ to equilibrium, the extracellular CA inhibitor ACZ totally blocked extracellular CA enzyme activity.

Assessing RBC Hemolysis

Figure 5C:
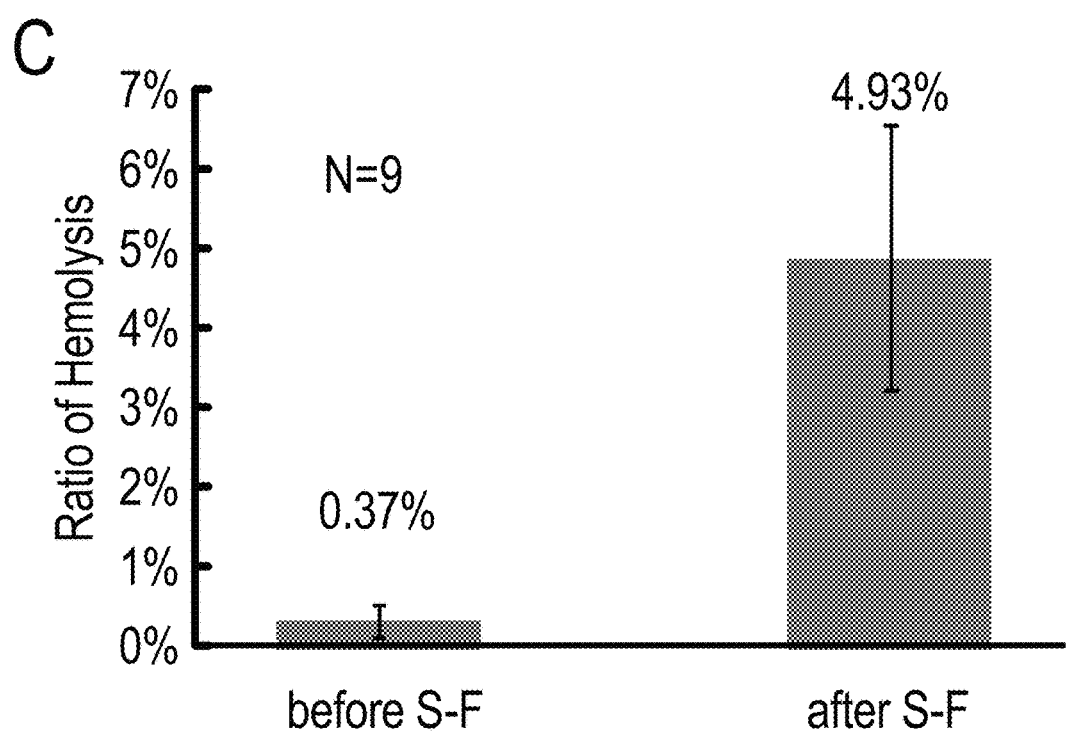
FIGS. 5(A-C) illustrate plots and a graph assessing RBC hemolysis. A: Estimation of real hemolysis with 100% intact RBCs (HCT≅0.37%). B: Calculation of real hemolysis of 100% intact RBCs. C: Comparison of hemolysis with 100% intact RBCs (HCT≅0.3%) before and after Stopped-flow machine.

We collected fresh blood from mouse by cardiac puncture method. Before used as intact RBCs for further experiments, RBCs were washed for four times with the final hemolysis of RBCs around 0.37%±0.21% (SD) (FIG. 5A). Using method in FIG. 5B, we compared the results of FIG. 3C and FIG. 4C and concluded that—even when working with RBCs from wt mice—about ~4.93%±1.67% (SD) of the RBCs were hemolyzed in the SF cell. This result was compared with ~0.37%±0.21% (SD) hemolysis before the RBCs enter the SF device (FIG. 5C). Thus, the rapid mixing of RBCs in the SF cell increases hemolysis.

Our CA assay is a novel method for assessing RBC fragility, based on the first use of out-of-equilibrium (OOE) $CO_2/HCO_3^-$ solutions in a Stopped Flow device in 10° C. In our protocol, the mixed two OOE solutions are HEPES buffer (pH 7.03 at 10° C.) and $HCO_3^-$ buffer (pH 8.41, ~1% $CO_2$). When performing CA assay, murine RBCs were mixed in HEPES buffer with pH of 7.03, $pH_o$ at the instant of mixing is about 7.25 and finally the reaction $HCO_3^- + H^+ \rightarrow CO_2 + H_2O$ causes $pH_o$ to rise to about 7.50. During this process, carbonic anhydrase (CA) rapidly catalyzes the reaction and causes a pH shift to reach equilibrium. 10° C. was used in this study to keep RBCs under a condition close to physiological and at the same time maintain a suitable CA enzyme catalyzing reaction rate.

The development of a physiological, rapid, and reliable assay can be used for assessing the fragility and/or identifying the fraction of intact RBCs when studying the transport properties of RBCs or utilizing stored blood for transfusion. In intact RBCs there is a very low but measurable CA activity, however, upon lysis and release of CAI and CAII, this activity is greatly increased. Monitoring CA activity offers another advantage because the reversible reaction mechanism—$H^+ + HCO_3^- \leftrightarrow H_2CO_3 \leftrightarrow CO_2 + H_2O$—can consume or produce a proton. For example, in the presence of $HCO_3^-$ there is a net alkalinization due to the consumption of a proton. While on the other hand, in the presence of $CO_2$, there is a net acidification due to the production of a proton. Thus, during catalysis it is possible to monitor a change in extracellular pH ($\Delta pH_0$) in either direction depending on which substrate is present.

Calibration of Dye

Pyranine (HPTS) was selected as a suitable fluorescent pH-indicator for its good properties and has been used as extracellular pH indicator for its lack of cell permeability. So we performed experiments to obtain the pH calibration curve for HPTS. The pk value we got in 10° C. for pyranine was 7.11±0.01(SD). In previous study, PKa of HPTS is around 7.3.

Using Purified Bovine CA II for CA Assay

In RBCs, there are two main cytoplasmic isoforms of carbonic anhydrase, CA I and CA II. They catalyze the reaction $HCO_3^- + H^+ \leftarrow \rightarrow H_2CO_3 \leftarrow \rightarrow CO_2 + H_2O$ and are important for carrying metabolically produced $CO_2$ from the systemic tissues to the pulmonary capillaries for elimination in the exhaled air. Though there are almost 89% of CA I in RBCs, the enzyme activity of CA II is several times higher than that of CA I. We first selected commercial purified bovine CAII to perform the experiment. As shown in FIG. 2 FIGS. 2A and 2B, the greater the concentration of CA II, the faster the reaction to equilibrium, with $pH_o$ changed from initial mixing of ~7.25 to 7.5. The dependence of $k_{rx}$ on [CA II] is linear (FIG. 2C).

CA Assay on Mouse Hemolysate

We hypothesized that we could exploit the release of carbonic anhydrase from RBCs to quantitate the degree of hemolysis. We combined varying amounts of freshly prepared, intact murine RBCs (~0.3% hematocrit) with RBC lysate, keeping the total hemoglobin constant at 5 μM to simulate different degrees of hemolysis (0-100%). At the same time, we use incremental amounts of RBC lysate without intact murine RBCs to mimic different degrees of hemolysis (relative amount of 0-100% hemoglobin). As shown in FIG. 3 FIGS. 2A & 3B and FIG. 4 FIGS. 2A & 4B, high % hemolysis with more CA released from RBCs compared with faster of reaction to get to equilibrium, with $pH_o$ changed from initial mixing of ~7.25 to 7.5. When mixing solution A with 0% hemolysis of 100% intact RBCs, the reaction $HCO_3^- + H^+ \rightarrow CO_2 + H_2O$ caused $pH_o$ to reach ~7.5 in ~100 s, which was faster than that of 0% hemolysis without intact RBCs (~200 s). FIG. 3C and FIG. 4C showed the summary of results in FIG. 3A and FIG. 4A. As expected, both dependence of $k_{rx}$ on % hemolysis were linear. For 0% hemolysis without intact RBCs, y-intercept was ~0.0183 s$^{-1}$ that was very close to the rate constant of the uncatalyzed reaction in FIG. 2C, while for 0% hemolysis with 100% intact RBCs, y-intercept was ~0.082 s$^{-1}$ that was higher than uncatalyzed reaction in FIG. 2C and FIG. 3C. This meaned partially hemolyzed of intact RBCs in the SF cell. By calculating, we concluded that though the initial hemolysis before loading into the SF machine was <1%, the estimated initial hemolysis in the OOE SF assay was ~4.93%, presumably due to mechanical forces of rapid mixing.

CA Assay with CA Inhibiter ACZ

We hypothesized that all the carbonic anhydrase catalyzing the reaction $HCO_3^- + H^+ \rightarrow CO_2 + H_2O$ are extracellular CA released from RBCs. In order to confirm this hypothesis, we added CA blocker acetazolamide (ACZ) in the solution opposite to CA. As expected, compared with no ACZ, adding ACZ significantly inhibited bCAII or RBCs released CA catalyzing reaction $HCO_3^- + H^+ \rightarrow CO_2 + H_2O$ and slowed $pH_o$ to reach ~7.5 in ~200 s (FIGS. 2D, 3D and 4D). ACZ also reduced $k_{rx}$ to the uncatalyzed value (~0.02 $s^{-1}$, FIGS. 2F, 3F and 4F), which meaned all CA activity to be extracellular.

Our CA assay is firstly to analyze hemolysis under approximately physiological condition. This assay is easy to perform, high precision, reproducible, and in principle could be applied to many other cell types.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention the following is claimed:

1. A method of measuring the amount or activity of carbonic anhydrase enzyme, in a bodily sample, the method comprising:
    mixing a bodily sample including RBC lysate with a first physiological $CO_2/HCO_3^-$ solution, the first physiological $CO_2/HCO_3^-$ solution having a pH of about 7;
    mixing the first physiological $CO_2/HCO_3^-$ solution, which includes the bodily sample, with a second $CO_2/HCO_3^-$ solution, which includes $NaHCO_3$, having a basic dissimilar pH; and
    measuring the rate at which the pH of the newly mixed solution equilibrates under the influence of the enzyme to determine carbonic anhydrase activity.

2. The method of claim 1, wherein the first physiological $CO_2/HCO_3^-$ solution and the second $CO_2/HCO_3^-$ solution are mixed in a stopped flow device.

3. The method of claim 1, wherein the rate at which the pH equilibrates is measured by adding a fluorescent pH indicator dye to the first physiological $CO_2/HCO_3^-$ solution and/or the second physiological $CO_2/HCO_3^-$ solution and measuring a change of fluorescence of the dye.

4. The method of claim 3, wherein the pH indicator dye is pyranine.

5. The method of claim 1, wherein the bodily sample includes red blood cells and an increase in enzyme or enzyme activity is indicative of increased red blood cell hemolysis.

6. The method of claim 5, wherein the red blood cells are from stored blood.

7. The method of claim 1, wherein the first physiological $CO_2/HCO_3^-$ solution is a 4-(2-hydroxyethyl)-1-piperazineethanesulfonic acid) buffered solution.

8. The method of claim 1, wherein the second physiological $CO_2/HCO_3^-$ solution has a pH of about 8.4 prior to mixing.

9. The method of claim 8, the first physiological $CO_2/HCO_3^-$ solution and the second physiological $CO_2/HCO_3^-$ solution having a temperature of about 10° C.

10. A method for detecting red blood cell hemolysis in a bodily sample, the method comprising:
    mixing a bodily sample including red blood cells (RBC) and/or RBC lysate with a first physiological $CO_2/HCO_3^-$ solution, the first physiological $CO_2/HCO_3^-$ solution having a pH of about 7;
    mixing the first physiological $CO_2/HCO_3^-$ solution, which includes the bodily sample, with a second $CO_2/HCO_3^-$ solution, which includes $NaHCO_3$, having a basic dissimilar pH; and
    measuring the rate at which the pH of the newly mixed solution equilibrates under the influence of the carbonic anhydrase enzyme in the bodily sample to determine red blood cell hemolysis in the bodily sample.

11. The method of claim 10, wherein the first physiological $CO_2/HCO_3^-$ solution and the second $CO_2/HCO_3^-$ solution are mixed in a stopped flow device.

12. The method of claim 10, wherein the rate at which the pH equilibrates is measured by adding a fluorescent pH indicator dye to the first physiological $CO_2/HCO_3^-$ solution and/or the second physiological $CO_2/HCO_3^-$ solution and measuring a change of fluorescence of the dye.

13. The method of claim 12, wherein the pH indicator dye is pyranine.

14. The method of claim 12, wherein the bodily sample includes red blood cells from stored blood.

15. The method of claim 10, wherein the first physiological solution is a 4-(2-hydroxyethyl)-1-piperazineethanesulfonic acid) solution.

16. The method of claim 10, wherein the second physiological $CO_2/HCO_3^-$ solution has a pH of about 8.4 prior to mixing.

17. The method of claim 16, the first physiological $CO_2/HCO_3^-$ solution and the second physiological $CO_2/HCO_3^-$ solution having a temperature of about 10° C.

18. A method for determining red blood cell hemolysis in a bodily sample, the method comprising:
    mixing a bodily sample including red blood cells (RBC) and/or RBC lysate with a first physiological $CO_2/HCO_3^-$ solution, the first physiological $CO_2/HCO_3^-$ solution having a pH of about 7;
    mixing the first physiological $CO_2/HCO_3^-$ solution with a second $CO_2/HCO_3^-$ solution having a pH of about 8.4;
    measuring the rate at which the pH of the newly mixed solution equilibrates under the influence of the carbonic anhydrase enzyme in the bodily sample to determine red blood cell hemolysis in the bodily sample.

* * * * *